United States Patent [19]

Goris

[11] Patent Number: 5,489,285
[45] Date of Patent: Feb. 6, 1996

[54] SURGICAL SAW BLADE AND CLAMP

[75] Inventor: Gregory A. Goris, Ojai, Calif.

[73] Assignee: Hall Surgical, Div. of Zimmer, Inc., Warsaw, Ind.

[21] Appl. No.: 200,342

[22] Filed: Feb. 23, 1994

[51] Int. Cl.$^6$ .................................. A61B 17/14
[52] U.S. Cl. ..................... 606/82; 606/176; D24/146
[58] Field of Search ................. 606/79, 82, 171, 606/176, 178, 177; 30/331, 344, 339; 403/373, 374, 409.1; D24/146; D8/64, 5

[56] References Cited

U.S. PATENT DOCUMENTS

| | | | |
|---|---|---|---|
| D. 343,247 | 1/1994 | Walen | D24/146 |
| 3,678,934 | 7/1972 | Warfield et al. | |
| 3,905,374 | 9/1975 | Winter | |
| 3,943,934 | 3/1976 | Bent | |
| 4,106,181 | 8/1978 | Mattchen | 29/450 R |
| 4,204,692 | 5/1980 | Hoffman | 279/81 |
| 4,252,121 | 2/1981 | Arnegger | |
| 4,285,129 | 8/1981 | Hoffman | 30/392 |
| 4,299,402 | 11/1981 | Hoffman | 279/75 |
| 4,386,609 | 6/1983 | Mongeon | |
| 4,513,742 | 4/1985 | Arnegger | |
| 4,584,999 | 4/1986 | Arnegger | |
| 4,617,930 | 10/1986 | Saunders | |
| 4,872,452 | 10/1989 | Alexson | |
| 5,178,626 | 1/1993 | Pappas | 606/178 |
| 5,263,972 | 11/1993 | Evans et al. | 606/176 |
| 5,265,343 | 11/1993 | Pascaloff | 30/339 |

OTHER PUBLICATIONS

Zimmer, Inc. brochure—Air Driver Blades–The Next Generation—Jun. 1993.
Zimmer, Inc. brochure—More Versatile "Graft" Blades Available—Feb. 1993.
Hall Surgical brochure—New Opposed–Tooth Blades—Prior to 1990.
Hall Surgical brochure—New Opposed–Tooth Blades—Published prior to Jan. 1, 1994.
Stryker Corporation brochure—Published prior to Jan. 1, 1994.

*Primary Examiner*—Tamara L. Graysay
*Assistant Examiner*—Scott B. Markow
*Attorney, Agent, or Firm*—Cary R. Reeves; Gene Warzecha

[57] ABSTRACT

A blade and clamp obtain a motion free coupling while remaining easily operable. The clamp comprises first and second clamping faces. The second clamping face includes a plurality of tapered lugs arranged in a radial pattern. The blade comprises a plate-like body having a primary U-shaped slot and a plurality of radial U-shaped slots which engage the tapered lugs of the clamp to produce a tight motion free coupling between the blade and clamp.

5 Claims, 3 Drawing Sheets

SURGICAL SAW BLADE AND CLAMP

BACKGROUND OF THE INVENTION

The present invention relates to a surgical saw blade and corresponding clamp.

Orthopaedic procedures often require the use of powered bone saws. Commonly used is the oscillating saw which rapidly moves a flat, plate-like blade through an arc in front of the saw body. These powered saws operate at high speed and with large blade loads. Therefore, it is important that the blade be coupled to the saw in such a way as to eliminate, as far as possible, relative motion between the blade and the saw since such motion results in vibration, wear, heat and power loss.

SUMMARY OF THE INVENTION

The blade and clamp of this invention provide a motion free coupling while at the same time providing for easy placement and removal of the blade in and from the clamp.

The clamp has a first clamping face mounted within a housing and a second clamping face mounted within the housing parallel to the first clamping face. The two clamping faces define a space for receiving the blade. The second clamping face includes a plurality of lugs projecting toward the first clamping face. Each lug comprises a rectangular base portion adjacent the second clamping face and end walls and converging side walls extending away from the second clamping face. The rectangular base portion of each lug has a base axis parallel to the side walls. The lugs are located with their base axes in a radial pattern about an axis perpendicular to the first and second clamping faces.

The blade comprises a plate-like body having relatively broad parallel side surfaces and a relatively narrow edge extending around the body. The blade has an end portion for engaging the clamp assembly, the end portion having a primary U-shaped through slot between the side surfaces and opening to the edge of the blade. The blade further includes a plurality of radial U-shaped through slots. Each radial slot has a longitudinal axis projecting radially from a common axis which is perpendicular to the side surfaces and each radial slot opens to the primary U-shaped slot.

When the blade is positioned within the clamp and one of the clamping faces is moved to reduce the space between the clamp faces, the lugs engage the radial U-shaped through slots. As the lugs increasingly engage the radial slots, the converging side walls abut the radial slots and cause the blade to seat tightly onto the angled sides of the lugs.

DETAILED DESCRIPTION OF THE INVENTION

Figure 1:
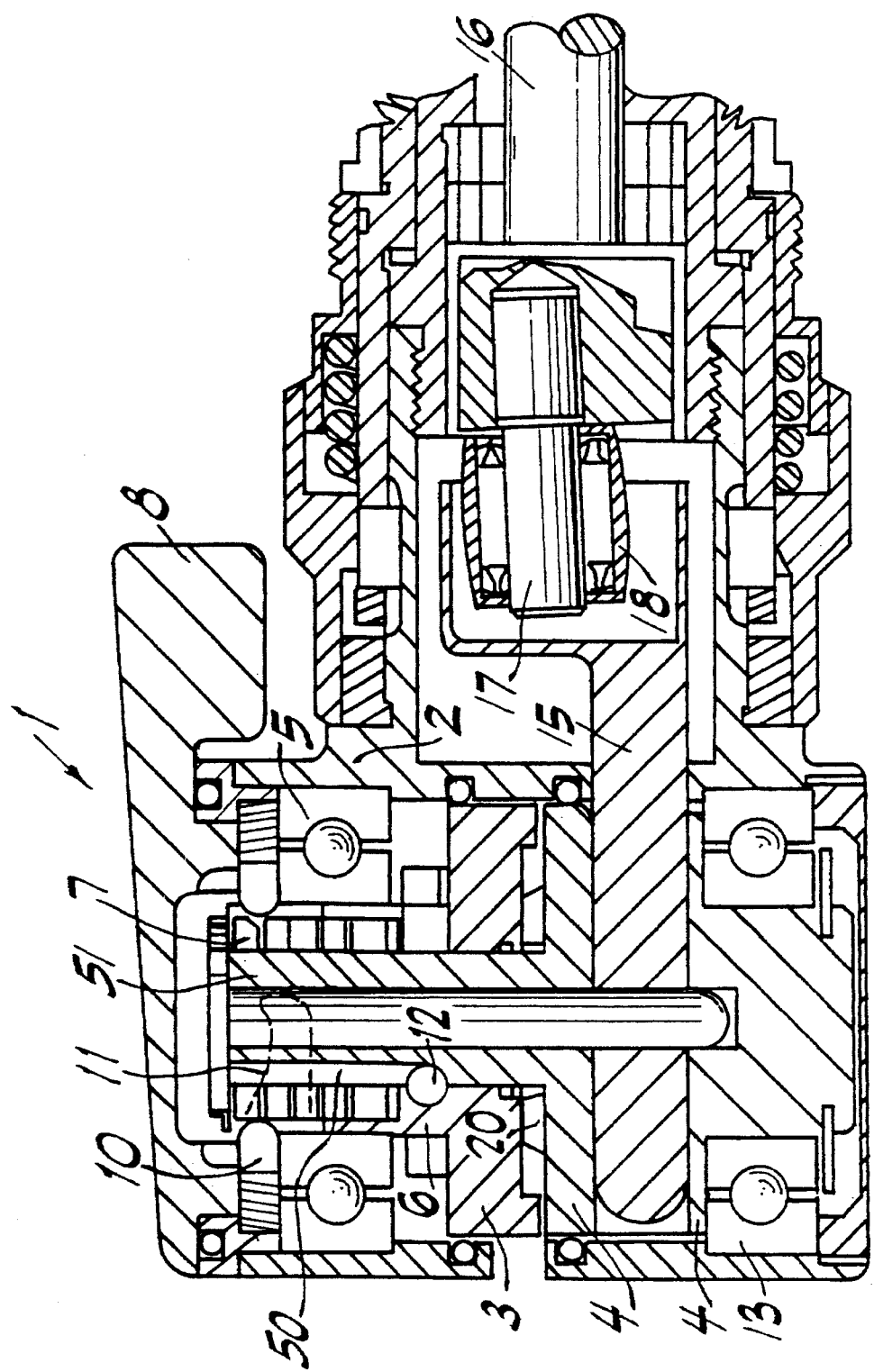
FIG. 1 is a side sectional view of the clamp of the present invention.

Referring to FIG. 1, a clamp assembly 1 for holding a plate-like blade in a powered bone saw includes a housing 2 and first 3 and second 4 clamping faces mounted within the housing and parallel to one another thereby defining a space between them.

The first clamping face 3 is rotatably mounted within the housing 2 by way of bearings 5 and a plunger 6. The plunger 6 is also capable of axial translation within the bearings 5 to increase and decrease the space between the clamping faces. A spring 7 biases the first clamping face 3 toward the second clamping face 4. A lever 8 is rotatably mounted on the housing 2 in axial alignment with the plunger 6. The lever 8 carries a pin 10. The plunger 6 contains an inclined slot 11 (shown in hidden lines) which engages the pin 10. When the lever 8 is rotated, the pin 10 rotates with it. As the pin 10 rotates, it moves within the inclined slot 11. However, the pin 10 is constrained within a horizontal plane so that as the pin 10 moves within the inclined slot 11 the plunger 6 moves upward thus moving the first clamping face 3 away from the second clamping face 4 and compressing the spring 7. The inclined slot 11 and the lever 8 together provide a mechanical advantage which magnifies a relatively low torsional force on the lever 8 into a relatively high compression force on the spring 7 so that high modulus springs can be used to provide high compression on the blade.

The second clamping face 4 is rotatably mounted within the housing 2 by way of bearings 13. A yoke 15 connects the second clamping face 4 to an input shaft 16. The input shaft 16 has an offset end 17 with an offset bearing 18. Rotation of the input shaft 16 causes the offset end 17 and offset bearing 18 to circumscribe a circular path. The yoke 15 follows the offset bearing 18 causing the second clamping face 4 to oscillate. The clamp faces 3 and 4 are locked to move together by use of an interlocking ball 12. The ball 12 is moveable in a groove 50 in the clamp extension 51 and held in place in a depression in the plunger 6.

Figure 2:
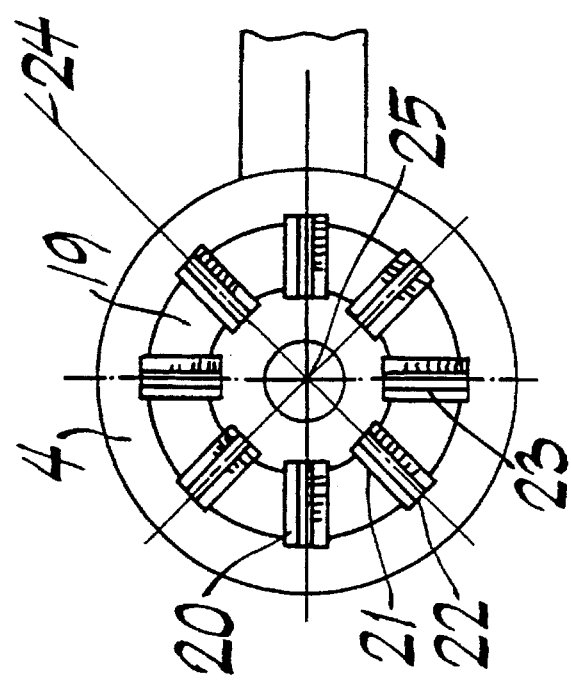
FIG. 2 is top view of the second clamping face of the clamp of FIG. 1.

Referring to FIG. 2, the second clamping face 4 includes a blade ring 19. The blade ring 19 comprises a plurality of connected lugs 20. The lugs 20 project away from the second clamping face 4 and toward the first clamping face 3. Each lug comprises an elongate base 21 portion adjacent the second clamping face 4. The base is preferably an elongate rectangular shape. End walls 22 and side walls 23 extend away from the second clamping face with the side walls 23 converging to form a truncated wedge. The elongate base portion 21 has a base axis 24 parallel to the side walls. The lugs 20 are located with their base axes 24 in a radial pattern about an axis 25 perpendicular to the first and second clamping faces.

Figure 3:
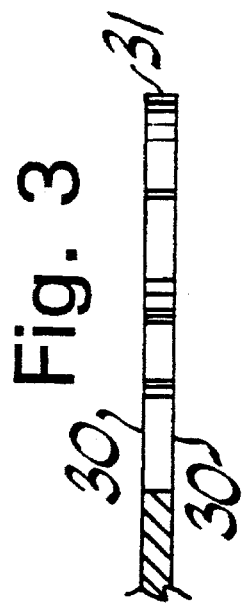
FIG. 3 is a side section view of the blade of the present invention.
Figure 4:
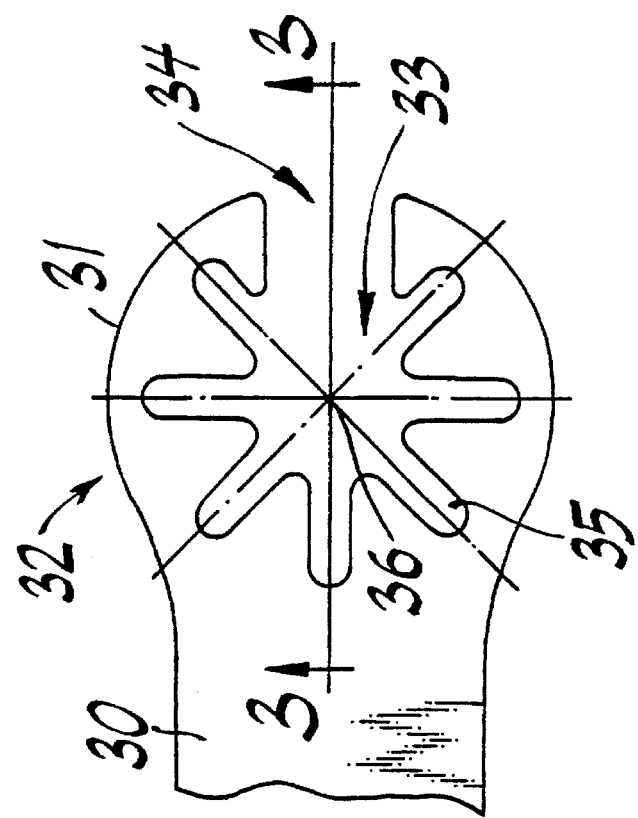
FIG. 4 is a top view of the blade of FIG. 3.

Referring to FIGS. 3 and 4, a blade for use with the above described clamp comprises a plate-like body having relatively broad parallel side surfaces 30 and a relatively narrow edge 31 extending around the body. An end portion 32 is adapted for engaging the clamp assembly. The end portion 32 has a primary U-shaped through slot 33 between the side surfaces and opening to the edge of the blade 34. The end portion 32 further includes a plurality of radial U-shaped through slots 35 arranged about an axis 36 which is perpendicular to the side surfaces 30. The radial slots 35 open to the primary U-shaped slot 33.

Figure 5:
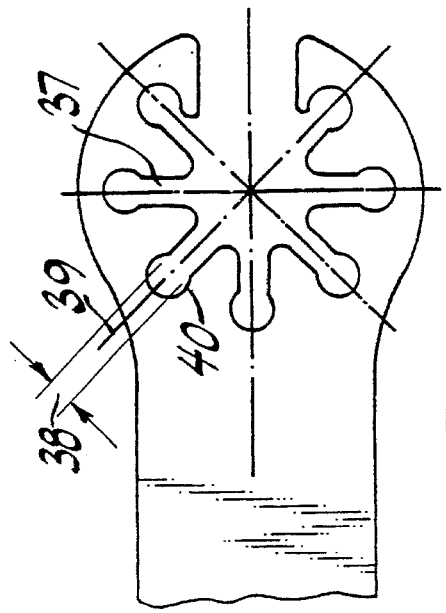
FIG. 5 is an alternative embodiment of the blade of FIG. 4.

FIG. 5 depicts an alternative embodiment of the blade of FIGS. 3 and 4 in which each radial U-shaped slot 37 has a width dimension 38 corresponding to the narrowest dimension perpendicular to its longitudinal axis 39 and parallel to the side surfaces 30. Each radial slot 37 further has a closed end 40 spaced from the primary U-shaped slot 33. The closed end 40 having a dimension wider than the width dimension 38 of the U-shaped slot. For example, the closed end 40 preferably forms a circular opening with a diameter larger than the width dimension 38 as shown. The alternative blade of FIG. 5 is useful where it is desired that the blade fit into the novel clamp of this invention as well as another clamp having circular pins for engaging the blade.

Figure 6:
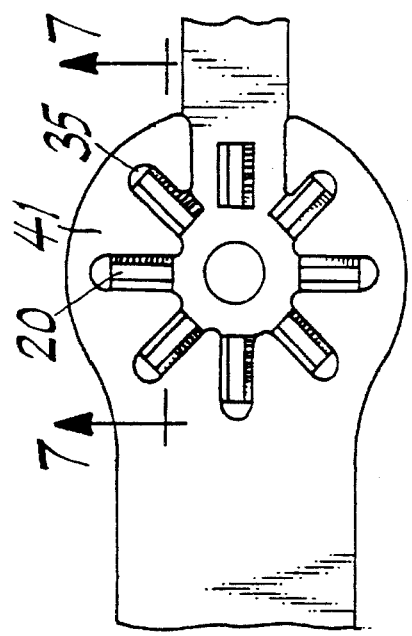
FIG. 6 is a top view of the blade of FIG. 3 seated on the second clamping face of FIG. 1.
Figure 7:
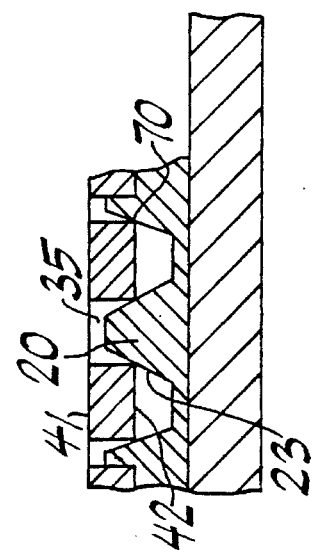
FIG. 7 is a sectional view of the blade and second clamping face of FIG. 6.
Figure 8:
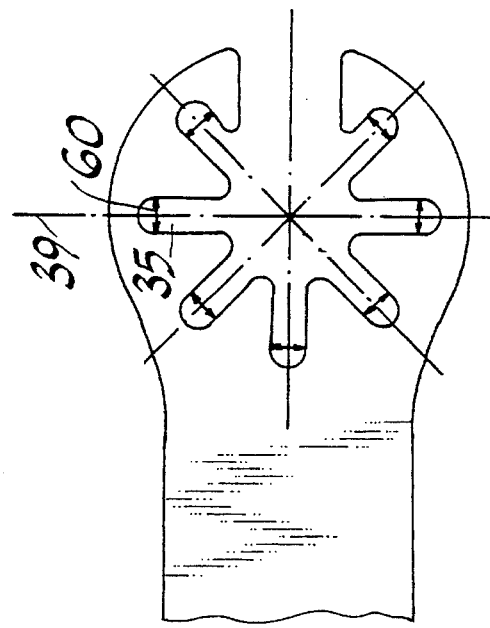
FIG. 8 is a top view similar to FIG. 4.

In use, the radial slots 35 of the blade engage the lugs 20 of the second clamping face 4 as shown in FIGS. 6 and 7. The first clamping face 3 presses against the top side surface 41 of the blade causing the radial slots 35 to engage the side walls 23 of the lugs 20. The radial slots 35 will engage the widening lugs 20 until the radial slots 35 are filled. Therefore, the clamp can accommodate blades with variations in slot dimensions and still grip such varying blades tightly. As the radial slots 35 engage the lugs 20, the lugs impart reaction forces 60 along the radial slots 35 directed normal to the longitudinal axes 39 of the radial slots 35 as depicted in FIG. 8. In the embodiment shown which has seven radial slots, the reaction forces are directed in the eight directions normal to the longitudinal axes of the radial slots. These reaction forces are represented as point loads shown as double headed arrows in FIG. 8, but are actually distributed along the bottom edge 70 of the radial slots 35. Because the reaction forces are directed in several directions, the blade is very stable in the clamp and the blade and clamp resist relative motion imposed by blade loads from any direction. In other words, pulling, pushing, and side loads on the blade are met by a supporting lug face and are countered in each instance by the diverging lug pattern. Also, because of the accommodating lug taper and radial lug pattern, blade loads are distributed evenly among the lugs.

A further advantage of this invention is increased safety. All of the moving parts of the clamp are contained within the housing. In use, the blade extends from the narrow slot in the front of the housing and the blade is the only exposed moving part. This lessens the likelihood of the saw operator being injured.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A clamp assembly for releasably attaching a blade to a powered bone saw, the clamp assembly comprising:
   a first clamping face; and
   a second clamping face parallel to the first clamping face and defining a space between the first and second clamping faces for receiving the blade, the second clamping face including a plurality of lugs projecting toward the first clamping face, each lug comprising an elongate base portion adjacent the second clamping face with end walls and converging side walls extending away from the second clamping face, the elongate base portion having a base axis parallel to the side walls, the lugs being located with their base axes in a radial pattern about an axis perpendicular to the first and second clamping faces, the base axes of at least two of the lugs diverging from being parallel to one another.

2. A clamp assembly for holding a plate-like blade in a powered bone saw, which blade has parallel side surfaces and an end portion having a U-shaped through slot between the side surfaces and opening to an edge of the blade, which blade further includes a plurality of radial through slots arranged about an axis which is perpendicular to the side surfaces, the clamp assembly comprising:
   a first clamping face; and
   a second clamping face parallel to the first clamping face and defining a space between the first and second clamping faces for receiving the blade, the second clamping face including a plurality of lugs projecting toward the first clamping face, each lug comprising an elongate base portion adjacent the second clamping face with end walls and converging side walls extending away from the second clamping face, the elongate base portion having a base axis parallel to the side walls, the lugs being located with their base axes in a radial pattern about an axis perpendicular to the first and second clamping faces, the base axes of at least two of the lugs diverging from being parallel to one another.

3. In combination:
   a plate-like blade comprising parallel side surfaces and an end portion having a primary U-shaped through slot between the side surfaces and opening to an edge of the blade, the blade further including a plurality of radial through slots arranged about an axis which is perpendicular to the side surfaces; and
   a clamp assembly comprising a first clamping face and a second clamping face and defining a space between the first and second clamping faces for receiving the blade, the second clamping face including a plurality of lugs projecting toward the first clamping face, each lug comprising an elongate base portion adjacent the second clamping face with end walls and side walls extending away from the second clamping face, the side walls converging toward a lug end portion, the lugs being located to engage the radial through slots when the blade is positioned within the clamp assembly, the lug base portions being wider than the through slots and the lug end portions being narrower than the through slots, one of the first and second clamping faces being movable to reduce the space between the first and second clamping faces and cause the lugs to engage the radial through slots.

4. A blade for attachment to a powered surgical saw via a clamp assembly, which clamp assembly has a first clamping face and a second clamping face defining a space for receiving the blade, the second clamping face including a plurality of lugs projecting toward the first clamping face, the blade comprising:
   a plate-like body having parallel side surfaces and an edge extending around the body and
   an end portion for engaging the clamp assembly, the end portion having a primary U-shaped through slot between the side surfaces and opening to the edge of the blade, the blade further including a plurality of radial U-shaped through slots arranged about an axis which is perpendicular to the side surfaces, each radial slot having an open end communicating with the primary U-shaped slot.

5. A blade for attachment to a powered surgical saw via a clamp assembly, the blade comprising:
   a plate-like body having parallel side surfaces and an edge extending around the body and
   an end portion for engaging the clamp assembly, the end portion having a primary U-shaped through slot between the side surfaces and opening to the edge of the blade, the blade further including a plurality of radial U-shaped through slots, each radial slot having a longitudinal axis projecting radially from a common axis which is perpendicular to the side surfaces, each radial slot having an open end communicating with the primary U-shaped slot.

* * * * *